US006421613B1

(12) United States Patent
Nadimpalli et al.

(10) Patent No.: US 6,421,613 B1
(45) Date of Patent: Jul. 16, 2002

(54) DATA PROCESSING OF THE MAIZE PROLIFERA GENETIC SEQUENCE

(75) Inventors: Ramgopal Nadimpalli, Bloomfield, NJ (US); Carl R. Simmons, Des Moines, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 55 days.

(21) Appl. No.: 09/604,605

(22) Filed: Jun. 27, 2000

Related U.S. Application Data
(60) Provisional application No. 60/143,222, filed on Jul. 9, 1999.

(51) Int. Cl.[7] ......................... G06F 19/00; G01W 33/48; C12Q 1/68
(52) U.S. Cl. ................ 702/20; 435/6; 702/19; 703/6; 703/11; 707/1
(58) Field of Search ................ 702/19, 20; 395/500.05, 395/500.23; 435/6; 703/6, 11; 707/1

(56) References Cited

PUBLICATIONS

Springer et al., Science, vol. 268, pp. 877–880, 1995.*
SWISSPROT Accession No. P43299 (Nov. 1, 1995).*
GenBank Accession No. L 39954 (Jun. 20, 1995).*

* cited by examiner

*Primary Examiner*—Ardin H. Marschel
*Assistant Examiner*—Amy Hartter
(74) *Attorney, Agent, or Firm*—David B. Ran; Herbert H. Jervis; Foley & Lardner

(57) ABSTRACT

The invention provides isolated prolifera nucleic acids and their encoded proteins. The present invention provides methods and compositions relating to altering prolifera levels in plants. The invention further provides recombinant expression cassettes, host cells, transgenic plants, and antibody compositions.

14 Claims, No Drawings

DATA PROCESSING OF THE MAIZE PROLIFERA GENETIC SEQUENCE

RELATED APPLICATONS

This application claims priority to U.S. Ser. No. 60/143,222, filed Jul. 9, 1999, which is incorporated herein by reference.

TECHNICAL FIELD

The present invention relates generally to plant molecular biology. More specifically, it relates to nucleic acids and methods for modulating their expression in plants.

BACKGROUND OF THE INVENTION

Genes encoding MCM proteins were originally reported from budding and fission yeast. Eukaryotic MCM sequences reported so far are homologous to any of the six MCM genes identified in yeast. Recently MCM proteins were reported in Archaea genomes as well, pointing to their ancient existence and critical role in several organisms.

MCM2-3-5 proteins are nuclear-localized in yeast and are required for DNA replication from specific replication origins. The MCM mutants exhibit defects in cell cycle progression in yeast. In Drosophila, mutations in MCM2 or MCM4 (dpa) inhibit cell proliferation and are lethal, with mutants showing prolonged S phase. In Arabidopsis following prolifera (PRL) gene disruption by transposon mutagenesis, semi-sterile plants with reduced megagametophyte viability were observed. Thus a clear role for the prolifera gene was established in plants in megagametophyte and embryo development.

At least in yeast, Xenopus, and mammals, there is a considerable amount of literature available about the MCM proteins and some models about their specific role at the molecular level in DNA replication. DNA replication is a very complex and tightly regulated process in eukaryotes and the machinery has been documented to be broadly conserved across eukaryotes. In eukaryotes, DNA replication actually is initiated from several replication origins and by some controlling mechanisms, that apparently involve other proteins, the replication process is restricted to a single round per each cell cycle. This ensures that cells do not end up with multiple sets of genomes resulting in polyploidy. Initiation of DNA replication follows the formation of a complex of proteins called Origin Recognition Complex (ORC) which may probably permit loading of other required proteins for the process such as cdc6 in yeast (cdc18 in *S. pombe*). Overexpression of cdc18 in *S. pombe* induces multiple rounds of S phase in the absence of mitosis and thus cdc6/cdc18 together ensure one round of DNA replication per cycle. Mutants of MCM proteins suggest that these proteins bind to chromatin in G1 phase and disassociate in S phase through the end of mitosis. This phase-specific association ensures that the replication origins remain competent only at the end of G1 phase and fire only once during S phase leading to one cycle of replication. In general, binding of MCM proteins to chromatin also require other proteins such as cdc6/cdc18 in conjunction possibly with some protein kinases cdk2/cdc2 and cdc7-dbf4 regulate firing of origins of replication.

Cell division plays a crucial role during all phases of plant development. The continuation of organogenesis and growth responses to a changing environment requires precise spatial, temporal and developmental regulation of cell division activity in meristems (and in cells with the capability to form new meristems, such as in lateral root formation). Such control of cell division is also important in organs themselves (i.e. separate from meristems per se), for example, in leaf expansion, secondary growth, and endoreduplication. It has been observed that endoreduplication occurs in about 20% of leaf epidermal cells in maize and in trichomes. In endosperm, endoreduplication has been well documented in maize. An important feature of cell differentiation in maize endosperm is nuclear enlargement through chromosome endoreduplication. This process may be related to many differentiation events, such as protein and starch synthesis and storage, accumulation of nucleotides, enzyme activation, and hormone synthesis, and consists of subsequent cycles of DNA replication without entering mitosis until high ploidy levels are attained. Variations in chromosome endoreduplication frequency in endosperm parenchyma have been described among maize populations.

What is needed in the art are methods and compositions to facilitate multiple rounds of DNA replication without nuclear division leading to polyploidy. Increasing the frequency of endoreduplication in the endospenn increases the size of endosperm cells and thus the endosperm size. Additionally, initiation of endoreduplication in leaf and stem cells, particularly in maize, leads to increased biomass and vegetative growth which has advantages in increasing plant yield. The present invention provides this and other advantages.

SUMMARY OF THE INVENTION

Generally, it is the object of the present invention to provide nucleic acids and proteins relating to the maize prolifera gene. It is an object of the present invention to provide: 1) antigenic fragments of the proteins of the present invention; 2) transgenic plants comprising the nucleic acids of the present invention; 3) methods for modulating, in a transgenic plant, the expression of the nucleic acids of the present invention.

Therefore, in one aspect, the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In another aspect, the present invention relates to recombinant expression cassettes, comprising a nucleic acid of the present invention operably linked to a promoter.

In another aspect, the present invention is directed to a host cell into which has been introduced the recombinant expression cassette.

In a further aspect, the present invention relates to an isolated protein comprising a polypeptide having a specified number of contiguous amino acids encoded by an isolated nucleic acid of the present invention.

In a further aspect, the present invention relates to a polynucleotide amplified from a *Zea mays* nucleic acid library using primers which selectively hybridize, under stringent hybridization conditions, to loci within polynucleotides of the present invention.

In another aspect, the present invention relates to an isolated nucleic acid comprising a polynucleotide of specified length which selectively hybridizes under stringent conditions to a polynucleotide of the present invention, or a complement thereof In some embodiments, the isolated nucleic acid is operably linked to a promoter.

In another aspect, the present invention relates to a recombinant expression cassette comprising a nucleic acid amplified from a library as referred to supra, wherein the nucleic acid is operably linked to a promoter. In some embodiments, the present invention relates to a host cell transfected with this recombinant expression cassette. In some embodiments, the present invention relates to a protein of the present invention that is produced from this host cell.

In yet another aspect, the present invention relates to a transgenic plant comprising a recombinant expression cassette comprising a plant promoter operably linked to any of the isolated nucleic acids of the present invention. The present invention also provides transgenic seed from the transgenic plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited throughout the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications,* D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M, Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). Thus, the maize preferred codon for a particular amino acid may be derived from known gene sequences from maize. Maize codon usage for 28 genes from maize plants is listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as filll-length. For example, the consensus sequence ANNNN AUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, *Antibodies, A Laboratoy Manual*, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "prolifera nucleic acid" is a nucleic acid of the present invention and means a nucleic acid comprising a polynucleotide of the present invention (a "prolifera polynucleotide") encoding a prolifera polypeptide. A "prolifera gene" is a gene of the present invention and refers to a heterologous genomic form of a full-length prolifera polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology,* Vol. 152, Academic Press, Inc., San Diego, Calif. (Berger); Sambrook et al., *Molecular Cloning—A Laboratory Manual,* 2nd ed., Vol. 1–3 (1989); and *Current Protocols in Molecular Biology,* F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays*.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucle-otides" as that term is intended herein. Moreover, DNAs or RNAs comprising unusual bases, such as inosine, or modified bases, such as tritylated bases, to name just two examples, are polynucleodides as the term is used herein. It will be appreciated that a great variety of modifications have been made to DNA and RNA that serve many useful purposes known to those of skdll in the art. The term polynucleotide as it is employed herein embraces such chemically, enznmatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, suifition, gamma-carboxylation of glutamnic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "issue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "prolifera polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "prolifera protein" is a protein of the present invention and comprises a prolifera polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed or not expressed at all as a result of deliberate human intervention. The term "recombinant" as used herein does not encompass the alteration of the cell or vector by naturally occurring events (e.g., spontaneous mutation, natural transformatior/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodes, A Laboratory Manual,* Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formarnide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.,* 138:267–284 (1984): $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formanide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecula Biology-Hybridization with Nucleic Acid Probes*, Part I, Chapter 2 "Overview of principles of hybridization and the strategy of nucleic acid probe assays", Elsevier, New York (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein. The following terms are used to describe the sequence relationships between a polynucleotide/polypeptide of the present invention with a reference polynucleotide/polypeptide: (a) "reference sequence", (b) "comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2: 482 (1981); by the homology alignment algorithm of Needleman and Wunsch, *J. Mol. Biol.* 48: 443 (1970); by the search for similarity method of Pearson and Lipman, *Proc. Natl. Acad Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16:10881–90 (1988); Huang, et al., *Computer Applications in the Biosciences* 8:155–65 (1992), and Pearson, et al., *Methods in Molecular Biology* 24: 307–331(1994).

The BLAST family of programs which can be used for database sinilarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995); Altschul et al., *J. Mol. Biol.*, 215:403–410 (1990); and, Altschul et al., *Nucleic Acids Res.* 25:3389–3402 (1997).

Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=4, and a comparison of both strands. For amino acid sequences, the BLASTP program uses as defaults a wordlength (W) of 3, an expectation (E) of 10, and the BLOSUM62 scoring matrix (see Henikoff& Henikoff (1989) *Proc. Natl. Acad Sci. USA* 89:10915).

In addition to calculating percent sequence identity, the BLAST algorithm also performs a statistical analysis of the similarity between two sequences (see, e.g., Karlin & Altschul, *Proc. Nat'l. Acad Sci. USA* 90:5873–5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.,* 17:149–163 (1993)) and XNU (Claverie and States, *Comput. Chem.,* 17:191–201 (1993)) low-complexity filters can be employed alone or in combination.

Unless otherwise stated, nucleotide and protein identity/similarity values provided herein are calculated using GAP (GCG Version 10) under default values.

GAP (Global Alignment Program) can also be used to compare a polynucleotide or polypeptide of the present invention with a reference sequence. GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 100. Thus, for example, the gap creation and gap extension penalties can each independently be: 0, 1, 2, 3, 4, 5, 6, 7, 8, 9, 10, 15, 20, 30, 40, 50, 60 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad Sci. USA* 89:10915).

Multiple alignment of the sequences can be performed using the CLUSTAL method of alignment (Higgins and Sharp (1989) *CABIOS.* 5:151–153) with the default parameters (GAP PENALTY=10, GAP LENGTH PENALTY=10). Default parameters for pairwise alignments using the CLUSTAL method are KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.,* 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched position s by the total number of positions in the window of comparison and multiplying the result by 100 to yield the percentage of sequence identity.

DETAILED DESCRIPTION OF THE INVENTION

Overview

The present invention provides, a mong other things, a maize gene called "Prolifera", represented by a cDNA, and methods for its use in improving crop plants. This gene belongs to the known MCM2-3-5 family of proteins. Compositions and methods for modulating (i.e., increasing or decreasing) the level of prolifera polynucleotides and polypeptides in plants is also provided. In particular, the polynucleotides and polypeptides of the present invention can be expressed temporally or spatially, e.g., at developmental stages, in tissues, and/or in quantities, which are uncharacteristic of non-recombinantly engineered plants. In addition to its role in increasing the frequency of endoreduplication, the present invention provides utility in such exemplary applications as the following:

Efficient Cell Transformton and DNA integration

Current transformation technology provides an opportunity to engineer plants with desired traits. Major advances in plant transformation have occurred over the last few years.

However, in many major crop plants, serious genotype limitations still exist. Transformation of some agronomically important crop plants continues to be both difficult and time consuming. For example, it is difficult to obtain a culture response from some maize varieties. Typically, a culture.response amenable to plant transformation has been obtained by optimizing medium components and/or explant material and source. This has led to success in some genotypes. While, transformation of model genotypes is efficient, the process of introgressing transgenes into production inbreds is laborious, expensive and time consuming. It would save considerable time and money if genes could be introduced into and evaluated directly in commercial parent lines and their hybrids.

There is evidence that cells must be dividing for transformation to occur. It has also been observed that dividing cells represent only a fraction of cells that transiently express a transgene. It will be relevant to mention that about 85% of cells in the explants used are generally in G1 phase, about 10% in G2 phase and only about 5% in S phase. Furthermore, the presence of damaged DNA in non-plant systems (similar to DNA introduced by particle gun or other physical means) has been well documented to rapidly induce cell cycle arrest. Methods for increasing the number of dividing cells by would therefore provide valuable tools for increasing transformation efficiency.

Current methods for genetic engineering in maize require a specific cell type as the recipient of new DNA. These cells are found in relatively undifferentiated, rapidly growing callus cells or on the scutellar surface of the immature embryo (which can be induced to give rise to callus). Irrespective of the delivery method currently used, DNA is introduced into literally thousands of cells, yet transformants are recovered at requencies of $10^{-5}$ relative to transiently-expressing cells. Exacerbating this problem, the trauma that accompanies DNA introduction directs recipient cells into cell cycle arrest and accumulating evidence suggests that many of these cells are directed into apoptosis or programmed cell death. Therefore it would be desirable to provide improved methods capable of increasing transformation efficiency in a number of cell types. Reports indicate that over expression of any of MCM genes typically enhances DNA replication. Therefore, the prolifera genes of the present invention, when overexpressed in plant cells, provide for increasing the frequency of dividing cells in explants used for transformation.

Selective Gene Amplification

Replication control can be modified on a more local level, thereby allowing specific replication origins in some parts of the genome to be activated repeatedly providing a selective advantage for gene amplification. In Drosophila, chondrion genes have been shown to be selectively amplified by this process. By selectively expressing a prolifera polynucleotide of the present invention with the Origin Recognitoin Complex (ORC), at a set of replication origins of specific genes, copy number in cells can be controlled. These replication origins can be placed on artificial chromosomes or plasmid-like elements, so that the genes contained therein are selectively amplified. This will offer unique opportunities for crop breeding of transgenic plants and coordinate stacking of multiple transgenes. This selective amplification can also be used to enhance the level of the gene product expression. Selective gene amplification can be used to control cosuppression, depending upon the circumstances, either to maintain the enhanced expression of a gene, or to shut a gene off, such as an endogenous one whose expression is not desired. Tissue-specific or developmental stage-specific or chemical inducible-specific expression of the maize prolifera gene or other factors controlling the ORC, could result in correspondingly specific control of gene expression and the traits that results from that expression. This will be extremely useful in stacking interesting transgenes in a particular genetic background.

Other Aspects of the Present Invention

The present invention also provides isolated nucleic acids comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme fuinction, or for use as immunogens or antigens to obtain antibodies specifically immunoreactive with a protein of the present invention. Such antibodies can be used in assays for expression levels, for identifring and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particula ly monocots such as the species of the family Gramineae including Hordeum, Secale, Triyicum, Sorghum (e.g., S. bicolor) and Zea (e.g., Z. mays). The isolated nucleic acid and proteins of the present invention can also be used in species from the genera: Cucurbinta Rosa, Vitis, Juglas, Fragaria, Lotus, Meadicago, Onobiychis, Tusdinoum, Trigonexr, Vigna, Citrus, Linum, Geranium, Manihoio Daucus, Arabidopsis, Brassica, invhanus, Sinapis, Airopa, Capsicum, Daturae Hyoscyamus, Lycopersicon, Nicotiana, Solarium, Petunia, Digitalis, Majorana, Ciahorium, Helianthus, Lactuca, Bromus, Aofoprag usr Antirrhinum, Heterocaflls, Nemesis, Pelargonium, Panieum, Pennisetum, Ranunculus, Senecio, Salpiglossis, Cucumis,, Brawallia, Glycine, Pisum, Phaseolus, Lolium, Oryza, and Avena.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:
(a) a polynucle otide encoding a polypeptide of SEQ ID NO: 2 and conservatively modified and polymorphic variants thereof, including exempa polynucleotides of SEQ ID NO: 1;
(b) an isolated polynucleotide which is the product of amplification from a plant nucleic acid library using primer pairs which selectively hybridize under stringent conditions to loci within a polynucleotide of the present invention;
(c) an isolated polynucleotide which selectively hybridizes to a polynucleotide of (a) or
(d) an isolated polynucleotide having a specified sequence identity with polynucleotides of (a), (b), or (c);
(e) an isolated polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;
(f) complementary sequences of polynucleotides of (a), (b), (c), (d), or (e); and
(g) an isolated polynucleotide comprising at least a specific number of contiguous nucleotides from a polynucleotide of (a), (b), (c), (d), (e), or (f);
(h) an isolated polynucleotide from a full-length enriched cDNA library having the physico-chemical property of selectively hybridizing to a polynucleotide of (a), (b), (c), (d), (e), (f, or (g);
(i) an isolated polynucleotide made by the process of: 1) providing a full-length enriched nucleic acid library, 2) selectively hybridizing the polynucleotide to a polynucleotide of (a), (b), (c), (d), (e), (f), (g), or (h), thereby isolating the polynucleotide from the nucleic acid library.

A. Polynucleotides Encoding A Polypeptide of the Present Invention

As indicated in (a), above, the present invention provides isolated nucleic acids comprising a polynucleotide of the present invention, wherein the polynucleotide encodes a polypeptide of the present invention. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Thus, each silent variation of a nucleic acid which encodes a polypeptide of the present invention is implicit in each described polypeptide sequence and is within the scope of the present invention. Accordingly, the present invention includes polynucleotides of the present invention and polynucleotides encoding a polypeptide of the present invention.

B. Polynucleotides Amplified from a Plant Nucleic Acid Library

As indicated in (b), above, the present invention provides an isolated nucleic acid comprising a polynucleotide of the present invention, wherein the polynucleotides are amplified, under nucleic acid amplification conditions, from a plant nucleic acid library. Nucleic acid amplification conditions for each of the variety of amplification methods are well known to those of ordinary skill in the art. The plant nucleic acid library can be constructed from a monocot such as a cereal crop. Exemplary cereals include corn, sorghum, alfalfa, canola, wheat, or rice. The plant nucleic acid library can also be constructed from a dicot such as soybean. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). Wheat lines are available from the Wheat Genetics Resource Center (Manhattan, Kans.).

The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using an enriched full-length cDNA synthesis method. Examples of such methods include Oligo-Capping (Maruyama, K. and Sugano, *S. Gene* 138: 171–174, 1994), Biotinylated CAP Trapper (Carninci, et al. *Genomics* 37: 327–336, 1996), and CAP Retention Procedure (Edery, E., Chu, L. L., et al. *Molecular and Cellular Biology* 15: 3363–3371, 1995). Rapidly growing tissues or rapidly dividing cells are preferred for use as an mRNA source for construction of a cDNA library. Growth stages of corn is described in "How a Corn Plant Develops," Special Report No. 48, Iowa State University of Science and Technology Cooperative Extension Service, Ames, Iowa, Reprinted February 1993.

A polynucleotide of this embodiment (or subsequences thereof) can be obtained, for example, by using amplification primers which are selectively hybridized and primer extended, under nucleic acid amplification conditions, to at least two sites within a polynucleotide of the present invention, or to two sites within the nucleic acid which flank and comprise a polynucleotide of the present invention, or to a site within a polynucleotide of the present invention and a site within the nucleic acid which comprises it. Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and Current Protocols in Molecular Biology, Unit 15.6, Ausubel, et al., Eds., Greene Publishing and Wiley-Interscience, New York (1995); Frohman and Martin, *Techniques* 1:165 (1989).

Optionally, the. primers are complementary to a subsequence of the target nucleic acid which they amplify but may have a sequence identity ranging from about 85% to 99% relative to the polynucleotide sequence which they are designed to anneal to. As those skilled in the art will appreciate, the sites to which the primer pairs will selectively hybridize are chosen such that a single contiguous nucleic acid can be formed under the desired nucleic acid amplification conditions. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art. The resulting translation products can be confirmed as polypeptides of the present invention by, for example, assaying for the appropriate catalytic activity (e.g., specific activity and/ or substrate specificity), or verifying the presence of one or more epitopes which are specific to a polypeptide of the present invention. Methods for protein synthesis from PCR derived templates are known in the art and available commercially. See, e.g., Amersham Life Sciences, Inc, Catalog '97, p.354.

C. Polynucleotides which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: maize, canola, soybean, cotton, wheat, sorghum, sunflower, alfalfa, oats, sugar cane, millet, barley, and rice. The cDNA library comprises at least 50% to 95% full-length sequences (for example, at least 50%, 60%, 70%, 80%, 90%, or 95% full-length sequences). The cDNA libraries can be normalized to increase the representation of rare sequences. See, e.g., U.S. Pat. No. 5,482,845. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% to 80% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. Identity can be calculated using, for example, the BLAST, CLUSTALW, or GAP algorithms under default conditions. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment comprise nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 97/20078. See also, U.S. Pat. Nos. 5,658,754; and 5,643,768. Peptide display libraries, vectors, and screening kits are commercially available from such suppliers as Invitrogen (Carlsbad, Calif.).

E. Polnucleotides Encoding a Protein Having a Subsequence from a Prototype Polypeptide and Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determiination of $k_{cat}$, $K_m$ and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of Thus, for example, polynucleotides of the present invention are inclusive of polynucleotides comprising at least 15, 20, 25, 30, 40, 50, 60, 75, or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

Subsequences can be made by in vitro synthetic, in vitro biosynthetic, or in vivo recombinant methods. In optional embodiments, subsequences can be made by nucleic acid amplification. For example, nucleic acid primers will be constructed to selectively hybridize to a sequence (or its complement) within, or co-extensive with, the coding region.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

H. Polynucleotides from a Full-length Enriched cDNA Library having the Physico-Chemical Property of Selectively Hybridizing to a Polynucleotide of (A)–(G)

As indicated in (h), above, the present invention provides an isolated polynucleotide from a full-length enriched cDNA library having the physico-chemical property of selectively hybridizing to a polynucleotide of paragraphs (A), (B), (C), (D), (E), (F), or (G) as discussed above. Methods of constructing full-length enriched cDNA libraries are known in the art and discussed briefly below. The cDNA library comprises at least 50% to 95% full-length sequences (for example, at least 50%, 60%, 70%, 80%, 90%, or 95% full-length sequences). The cDNA library can be constructed from a variety of tissues from a monocot or dicot at a variety of developmental stages. Exemplary species include maize, wheat, rice, canola, soybean, cotton, sorghum, sunflower, alfalfa, oats, sugar cane, millet, barley, and rice. Methods of selectively hybridizing, under selective hybridization conditions, a polynucleotide from a full-length enriched library to a polynucleotide of the present invention are known to those of ordinary skill in the art. Any number of stringency conditions can be employed to allow for selective hybridization. In optional embodiments, the stringency allows for selective hybridization of sequences having at least 70%, 75%, 80%, 85%, 90%, 95%, or 98% sequence identity over the length of the hybridized region. Full-length enriched cDNA libraries can be normalized to increase the representation of rare sequences.

I. Polynucleotide Products Made by a cDNA Isolation Process

As indicated in (I), above, the present invention provides an isolated polynucleotide made by the process of: 1) providing a full-length enriched nucleic acid library, 2) selectively hybridizing the polynucleotide to a polynucleotide of paragraphs (A), (B), (C), (D), (E), (F), (G, or (H) as discussed above, and thereby isolating the polynucleotide from the nucleic acid library. Full-length enriched nucleic acid libraries are constructed as discussed in paragraph (G) and below. Selective hybridization conditions are as discussed in paragraph (G). Nucleic acid purification procedures are well known in the art. Purification can be conveniently accomplished using solid-phase methods; such methods are well known to those of skill in the art and kits are available from commercial suppliers such as Advanced Biotechnologies (Surrey, UK). For example, a polynucleotide of paragraphs (A)–(H) can be immobilized to a solid support such as a membrane, bead, or particle. See, e.g., U.S. Pat. No. 5,667,976. The polynucleotide product of the present process is selectively hybridized to an immobilized polynucleotide and the solid support is subsequently isolated from non-hybridized polynucleotides by methods including, but not limited to, centrifugation, magnetic separation, filtration, electrophoresis, and the like.

Construction of Nucleic Acids

The isolated nucleic acids of the present invention can be made using (a) standard recombinant methods, (b) synthetic techniques, or combinations thereof In some embodiments, the polynucleotides of the present invention will be cloned, amplified, or otherwise constructed from a monocot such as corn, rice, or wheat, or a dicot such as soybean.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1999 (La Jolla, Calif.); and, Amersham Life Sciences, Inc, Catalog' 99 (Arlington Heights, Ill.).

A. Recombinant Methodsfor Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. Isolation of RNA, and construction of cDNA and genomic libraries is well known to those of ordinary skill in the art. See, e.g., *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995).

A1. Full-length Enriched cDNA Libraries

A number of cDNA synthesis protocols have been described which provide enriched full-length cDNA libraries. Enriched full-length cDNA libraries are constructed to comprise at least 600%, and more preferably at least 70%, 80%, 90% or 95% full-length inserts amongst clones containing inserts. The length of insert in such libraries can be at least 2,3, 4, 5, 6, 7, 8, 9, 10 or more kilobase pairs. Vectors to accommodate inserts of these sizes are known in the art and available commercially. See, e.g., Stratagene's lambda ZAP Express (cDNA cloning vector with 0 to 12 kb cloning capacity). An exemplary method of constructing a greater than 95% pure full-length cDNA library is described by Carninci et al, *Genomics*, 37:327–336 (1996). Other methods for producing full-length libraries are known in the art. See, e.g., Edery et al., *Mol. Cell Biol.*, 15(6):3363–3371 (1995); and, PCT Application WO 96/34981.

A2. Normalized or Subtracted cDNA Libraries

A non-normalized cDNA library represents the MRNA population of the tissue it was made from. Since unique clones are out-numbered by clones derived from highly expressed genes their isolation can be laborious. Normalization of a cDNA library is the process of creating a library in which each clone is more equally represented. Construction of normalized libraries is described in Ko, *Nucl. Acids. Res.*, 18(19):5705–5711 (1990); Patanjali et al., *Proc. Natl. Acad. U.S.A.*, 88:1943–1947 (1991); U.S. Pat. 5,482,685, 5,482,845, and 5,637,685. In an exemplary method described by Soares et al, normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8): 1954 (1991). cDNA subtraction kits are commercially available. See, e.g., PCR-Select (Clontech, Palo Alto, Calif.).

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning*

*Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. The T4 gene 32 protein (Boehringer Mannheim) can be used to improve yield of long PCR products.

PCR-based screening methods have been described. Wilfinger et al. describe a PCR-based method in which the longest cDNA is identified in the first step so that incomplete clones can be eliminated from study. *BioTechniques*, 22(3): 481–486 (1997). Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et at, *Meth. Enzymol.* 68: 90–99 (1979); the phosphodiester method of Brown et al, *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.,* 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill. In a particularly preferred embodiment, the ubiquitin 1 promoter is employed.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, New York (1994); *Corn and Corn Improvement,* 3rd edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that does not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, New York, (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227 1983. In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, New York (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene, 61:1–11 (1987) and Berger et al., Proc. Natl. Acad. Sci. U.S.A., 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al, *Proc. Nat'l. Acad Sci.* (*USA*) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., et al., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a ull-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5. The present invention further provides a protein comprising a polypeptide having a specified sequence identity with a polypeptide of the present invention. The percentage of sequence identity is an integer selected from the group consisting of from 60 to 99. Exemplary sequence identity values include 60%, 65%, 70%, 75%, 80%, 85%, 90%, and 95%.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and-translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., *Nature* 198:1056 (1977)), the tryptophan (trp) promoter system (Goeddel et al., *Nucleic Acids Res.* 8:4057 (1980)) and the lambda derived P L promoter and N-gene ribosome binding site (Shimatake et al., *Nature* 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics,* Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV ik promoter or pgk (phosphoglycerate kinase) promoter), an enhancer (Queen et al., *Immunol. Rev.* 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol.* 27: 353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in *DNA Cloning Vol. II a Practical Approach,* D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polypeptide of the present invention, for example a cDNA or a genornic sequence encoding a full length protein, will be used to construct a recombinant expression cassette which can be introduced into the desired plant. Isolated nucleic acid acids of the present invention can be introduced into plants according to techniques known in the art. Generally, recombinant expression cassettes as described above and suitable for transformation of plant cells are prepared. Techniques for transforming a wide variety of higher plant species are well known and described in the technical, scientific, and patent literature. See, for example, Weising et al., *Ann. Rev. Genet.* 22: 421–477 (1988). For example, the DNA construct may be introduced directly into the genomic DNA of the plant cell using techniques such as electroporation, polyethylene glycol (PEG), poration, particle bombardment, silicon fiber delivery, or microinjection of plant cell protoplasts or embryogenic callus. In preferred embodiment particle bombardment is employed. See, e.g., Tomes, et al., Direct DNA Transfer into Intact Plant Cells Via Microprojectile Bombardment. pp.197–213 in Plant Cell, Tissue and Organ Culture, Fundamental Methods. eds. O. L. Gamborg and G. C. Phillips. Springer-Verlag Berlin Heidelberg New York, 1995.

In optional emobodiments, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. See, U.S. Pat. No. 5,591,616.

The introduction of DNA constructs using PEG precipitation is described in Paszkowski et al., *Embo J.* 3: 2717–2722 (1984). Electroporation techniques are described in Fromm et al., *Proc. Natl. Acad. Sci.* (USA) 82: 5824 (1985). Ballistic transformation techniques are described in Klein et al., *Nature* 327: 70–73 (1987). *Agrobacterium tumefaciens*-mediated transformation techniques are well described in the scientific literature. See, for example Horsch et al., *Science* 233: 496–498 (1984), and Fraley et al, *Proc. Natl. Acad. Sci.* (USA) 80: 4803 (1983). Although Agrobacterium is usefull primarily in dicots, certain monocots can be transformed by Agrobacterium. For instance, Agrobacterium transformation of maize is described in U.S. Pat. No. 5,550,318.

Other methods of transfection or transformation include (1) *Agrobacterium rhizogenes*-mediated transformation (see, e.g., Lichtenstein and Fuller In: Genetic Engineering, vol. 6, P W J Rigby, Ed., London, Academic Press, 1987; and Lichtenstein, C. P., and Draper, J,. In: DNA Cloning, Vol. II, D. M. Glover, Ed., Oxford, IRI Press, 1985), Application PCT/US87/02512 (WO 88/02405 published Apr. 7, 1988) describes the use of *A. rhizogenes* strain A4 and its Ri plasmid along with *A. tumefaciens* vectors pARC8 or pARC16 (2) liposome-mediated DNA uptake (see, e.g., Freeman et al., *Plant Cell Physiol.* 25: 1353 (1984)), (3) the vortexing method (see, e.g., Kindle, *Proc. Natl. Acad Sci., (USA)* 87: 1228 (1990).

DNA can also be introduced into plants by direct DNA transfer into pollen as described by Zhou et al., Methods in Enzymology, 101:433 (1983); D. Hess, *Intern Rev. Cytol.,* 107:367 (1987); Luo et al., *Plant Mol. Biol. Reporter,* 6:165 (1988). Expression of polypeptide coding genes can be obtained by injection of the DNA into reproductive organs of a plant as described by Pena et al., *Nature,* 325.:274 (1987). DNA can also be injected directly into the cells of immature embryos and the rehydration of desiccated embryos as described by Neuhaus et al., *Theor. Appl. Genet.,* 75:30 (1987); and Benbrook et al., *in Proceedings Bio Expo* 1986, Butterworth, Stoneham, Mass., pp. 27–54 (1986). A variety of plant viruses that can be employed as vectors are known in the art and include cauliflower mosaic virus (CaMV), geminivirus, brome mosaic virus, and tobacco mosaic virus.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology,* Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol.* 2: *Special Methods in Peptide Synthesis, Part A.;* Merrifield, et al., *J. Am. Chem. Soc.* 85: 2149–2156 (1963), and Stewart et al., *Solid Phase Peptide Synthesis,* 2nd ed, Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide) are known to those of skill.

Purification of Proteins

The proteins of the present invention may be purified by standard techniques well known to those of skill in the art.

Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice,* Springer-Verlag: New York (1982); Deutscher, *Guide to Protein Purification,* Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Transformed plant cells which are derived by any of the above transformation techniques can be cultured to regenerate a whole plant which possesses the transformed genotype. Such regeneration techniques often rely on manipulation of certain phytohormones in a tissue culture growth medium. For transformation and regeneration of maize see, Gordon-Kanun et al., *The Plant Cell,* 2:603–618 (1990).

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture,* Macmillan Publishing Company, New York, pp. 124–176 (1983); and Binding, *Regeneration of Plants, Plant Protoplasts,* CRC Press, Boca Raton, pp. 21–73 (1985).

The regeneration of plants containing the foreign gene introduced by Agrobacterium from leaf explants can be achieved as described by Horsch et al., *Science,* 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A),* 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof Such regeneration techniques are described generally in Klee et al., *Ann. Rev. of Plant Phys.* 38: 467–486 (1987). The regeneration of plants from either single plant protoplasts or various explants is well known in the art. See, for example, *Methods for Plant Molecular Biology,* A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook,* Freeling and Walbot, Eds., Springer, N.Y. (1994); *Corn and Corn Improvement,* $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the the ratio of the polypeptides of the present invention in a plant. The method comprises introducing into a plant cell a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance.

See, e.g., Clark, Ed., *Plant Molecular Biology: A Laboratory Manual.* Berlin, Springer-Verlag, 1997. Chapter 7. For molecular marker methods, see generally, "The DNA Revolution" in: Paterson, A. H., *Genome Mapping in Plants* (Austin, Tex., Academic Press/R. G. Landis Company, 1996) pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 7-methylguanosine cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' untranslated regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 96/19256. See also, Zhang, J.- H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phyla, or kingdoms. For example, a polynucleotide having a consensus sequence from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Machine Applications

The present invention provides machines, articles of manufacture, and processes for identifying, modeling, or analyzing the polynucleotides and polypeptides of the present invention. Identification methods permit identification of homologues of the polynucleotides or polypeptides of the present invention while modeling and analysis methods permit recognition of structural or functional features of interest.

A. Machines: Data Processing Systems

In one embodiment, the present invention provides a machine having: 1) a memory comprising data representing at least one genetic sequence, 2) a genetic identification, analysis, or modeling progran with access to the data, 3) a data processor which executes instructions according to the program using the genetic sequence or a subsequence thereof, and 4) an output for storing or displaying the results of the data processing.

The machine of the present invention is a data processing system, typically a digital computer. The term "computer" includes one or several desktop or portable computers, computer workstations, servers (including intranet or internet servers), mainframes, and any integrated system comprising any of the above irrespective of whether the processing, memory, input, or output of the computer is remote or local, as well as any networking interconnecting the modules of the computer. Data processing can thus be remote or distributed amongst several processors at one or multiple sites. The data processing system comprises a data processor, such as a central processing unit (CPU), which executes instructions according to an application program. As used herein, machines, articles of manufacture, and processes are exclusive of the machines, manufactures, and processes employed by the United States Patent and Trademark Office or the European Patent Office when data representing the sequence of a polypeptide or polynucleotide of the present invention is used for patentability searches.

The machine of the present invention includes a memory comprising data representing at least one genetic sequence. As used herein, "genetic sequence" refers to the primary sequence (i.e., amino acid or nucleotide sequence) of a polynucleotide or polypeptide of the present invention. The genetic sequence can represent a partial sequence from a full-length protein, genomic DNA, or full-length cDNA/mRNA. Nucleic acids or proteins comprising a genetic sequence that is identified, analyzed, or modeled according to the present invention can be cloned or synthesized.

As those of skill in the art will be aware, the form of memory of a machine of the present invention, or the particular embodiment of the computer readable medium, are not critical elements of the invention and can take a variety of forms. The memory of such a machine includes, but is not limited to, ROM, or RAM, or computer readable media such as, but not limited to, magnetic media such as computer disks or hard drives, or media such as CD-ROMs, DVDs, and the like. The memory comprising the data representing the genetic sequence includes main memory, a register, and a cache. In some embodiments the data processing system stores the data representing the genetic sequence in memory while processing the data and wherein successive portions of the data are copied sequentially into at least one register of the data processor for processing.

Thus, the genetic sequence stored in memory can be a genetic sequence created during computer runtime or stored beforehand. The machine of the present invention includes a genetic identification, analysis, or modeling program (discussed below) with access to the data representing the genetic sequence. The program can be implemented in software or hardware.

The present invention further contemplates that the machine of the present invention will reference, directly or indirectly, a utility or function for the polynucleotide or polypeptide of the present invention. For example, the utility/function can be directly referenced as a data element in the machine and accessible by the program. Alternatively, the utility/function of the genetic can be indirectly referenced to an electronic or written record. The function or utility of the genetic sequence can be a function or utility for the genetic sequence, or the data representing the sequence (i.e., the genetic sequence data). Exemplary function or utilities for the genetic sequence include: 1) its name (per International Union of Biochemistry and Molecular Biology rules of nomenclature) or the function of the enzyme or protein represented by the genetic sequence, 2) the metabolic pathway that the protein represented by the genetic sequence participates in, 3) the substrate or product or structural role of the protein represented by the genetic sequence, or, 3) the phenotype (e.g., an agronomic or pharmacological trait) affected by modulating expression or activity of the protein represented by the genetic sequence.

The machine of the present invention also includes an output for displaying, printing, or recording the results of the identification, analysis, or modeling performed using a genetic sequence of the present invention. Exemplary outputs include monitors, printers, or various electronic storage mechanisms (e.g., floppy disks, hard drives, main memory) which can be used to display the results or employed as a means to input the stored data into a subsequent application or device.

In some embodiments, data representing a genetic sequence of the present invention is a data element within a data structure. The data structure may be defined by the computer programs that define the processes of identification, modeling, or analysis (see below) or it may be defined by the programming of separate data storage and retrieval programs subroutines or systems. Thus, the present invention provides a memory for storing a data structure that can be accessed by a computer programmed to implement a process for identification, analysis, or modeling of a genetic sequence. The data structure, stored within memory, is associated with the data representing the genetic sequence and reflects the underlying organization and structure of the genetic sequence to facilitate program access to data elements corresponding to logical sub-components of the genetic sequence. The data structure enables the genetic sequence to be identified, analyzed, or modeled. The underlying order and structure of a genetic sequence is data representing the higher order organization of the primary sequence. Such higher order structures affect transcription, translation, enzyme kinetics, or reflects structural domains or motifs. Exemplary logical sub-components which constitute the higher order organization of the genetic sequence include but are not limited to: restriction enzyme sites, endopeptidase sites, major grooves, minor grooves, beta-sheets, alpha helices, open reading frames (ORFs), 5' untranslated regions (UTRs), 3' UTRs, ribosome binding sites, glycosylation sites, signal peptide domains, intron-exon junctions, poly-A tails, transcription initiation sites, translation start sites, translation termination sites, methylation sites, zinc finger domains, modified amino acid sites, preproprotein-proprotein junctions, proprotein-protein junctions, transit peptide domains, single nucleotide polymorphisms (SNPs), simple sequence repeats (SSRs), restriction fragment length polymorphisms (RFLPs), insertion elements, transmembrane spanning regions, and stem-loop structures.

In another embodiment, the present invention provides a data processing system comprising at least one data structure in memory where the data structure supports the accession of data representing a genetic sequence of the present invention. The system also comprises at least one genetic identification, analysis, or modeling program which directs the execution of instructions by the system using the genetic sequence data to identify, analyze, or model at least one data element which is a logical sub-component of the genetic sequence. An output for the processing results is also provided.

B. Articles of Manufacture: Computer Readable Media

In one embodiment, the present invention provides a data structure in a computer readable medium that contains data representing a genetic sequence of the present invention. The data structure is organized to reflect the logical structuring of the genetic sequence, so that the sequence can be analyzed by software programs capable of accessing the data structure. In particular, the data structures of the present invention organize the genetic sequences of the present invention in a manner which allows software tools to perform an identification, analysis, or modeling using logical elements of each genetic sequence.

In a further embodiment, the present invention provides a machine-readable media containing a computer program and genetic sequence data. The program provides instructions sufficient to implement a process for effecting the identification, analysis, or modeling of the genetic sequence data. The media also includes a data structure reflecting the underlying organization and structure of the data to facilitate program access to data elements corresponding to logical sub-components of the genetic sequence, the data structure being inherent in the program and in the way in which the program organizes and accesses the data.

An example of a data structure resembles a layered hash table, where in one dimension the base content of the sequence is represented by a string of elements A, T, C, G and N. The direction from the 5' end to the 3' end is reflected by the order from the position 0 to the position of the length of the string minus one. Such a string, corresponding to a nucleotide sequence of interest, has a certain number of substrings, each of which is delimited by the string position of its 5' end and the string position of its 3' end within the parent string. In a second dimension, each substring is associated with or pointed to one or multiple attribute fields. Such attribute fields contain annotations to the region on the nucleotide sequence represented by the substring.

For example, a sequence under investigation is 520 bases long and represented by a string named SeqTarget. There is a minor groove in the 5' upstream non-coding region from position 12 to 38, which is identified as a binding site for an enhancer protein HM-A, which in turn will increase the transcription of the gene represented by SeqTarget. Here, the substring is represented as (12, 38) and has the following attributes: [upstream uncoded], [minor groove], [HM-A binding] and [increase transcription upon binding by HM-A]. Similarly, other types of information can be stored and structured in this manner, such as information related to the whole sequence, e.g., whether the sequence is a full length viral gene, a mammalian house keeping gene or an EST from clone X, information related to the 3' down stream non-coding region, e.g., hair pin structure, and information related to various domains of the coding region, e.g., Zinc finger.

This data structure is an open structure and is robust enough to accommodate newly generated data and acquired knowledge. Such a structure is also a flexible structure. It can be trimmed down to a 1-D string to facilitate data mining and analysis steps, such as clustering, repeat-masking, and HMM analysis. Meanwhile, such a data structure also can extend the associated attributes into multiple dimensions. Pointers can be established among the dimensioned attributes when needed to facilitate data management and processing in a comprehensive genomnics knowledgebase. Furthermore, such a data structure is object-oriented. Polymorphism can be represented by a family or class of sequence objects, each of which has an internal structure as discussed above. The common traits are abstracted and assigned to the parent object, whereas each child object represents a specific variant of the family or class. Such a data structure allows data to be efficiently retrieved, updated and integrated by the software applications associated with the sequence database and/or knowledgebase.

C. Processes: Identification, Analysis, or Modeling

The present invention also provides a process of identifying, analyzing, or modeling data representing a genetic sequence of the present invention. The process comprises: 1) providing a machine having a hardware or software implemented genetic sequence identification, modeling, or analysis program with data representing a genetic sequence, 2) executing the program while granting it access to the genetic sequence data, and 3) displaying or outputting the results of the identification, analysis, or modeling. Data structures made by the processes of the present invention and embodied within a computer readable medium are also provided herein.

A further process of the present invention comprises providing a memory embodied with data representing a genetic sequence and developing within the memory a data structure associated with the data and reflecting the underlying organization and structure of the data to facilitate program access to data elements corresponding to logical sub-components of the sequence. A computer is programmed with a program containing instructions sufficient to implement the process for effecting the identification, analysis, or modeling of the genetic sequence and the program is executed on the computer while granting the program access to the data and to the data structure within the memory. The program results are outputted.

Identification, analysis, and modeling programs are well known in the art and available commercially. The program typically has at least one application to: 1) identify the structural role or enzymatic function of the gene which the genetic sequence encodes or is translated from, 2) analyzes and identifies higher order structures within the genetic sequence or, 3) model the physico-chemical properties of a genetic sequence of the present invention in a particular environment.

Included amongst the modeling/analysis tools are methods to: 1) recognize overlapping sequences (e.g., from a sequencing project) with a polynucleotide of the present invention and create an alignment called a "contig"; 2) identify restriction enzyme sites of a polynucleotide of the present invention; 3) identify the products of a T1 ribonuclease digestion of a polynucleotide of the present invention; 4) identify PCR primers with minimal self-complementarity; 5) compute pairwise distances between sequences in an alignment, reconstruct phylogentic trees using distance methods, and calculate the degree of divergence of two protein coding regions; 6) identify patterns such as coding regions, terminators, repeats, and other consensus patterns in polynucleotides of the present invention; 7) identify RNA secondary structure; 8) identify sequence motifs, isoelectric point, secondary structure, hydrophobicity, and antigenicity in polypeptides of the present invention; 9) translate polynucleotides of the present invention and backtranslate polypeptides of the present invention; and 10) compare two protein or nucleic acid sequences and identifying points of similarity or dissimilarity between them.

Identification of the function/utility of a genetic sequence is typically achieved by comparative analysis to a gene/protein database and establishing the genetic sequence as a candidate homologue (i.e., ortholog or paralog) of a gene/protein of known function/utility. A candidate homologue has statistically significant probability of having the same biological function (e.g., catalyzes the same reaction, binds to homologous proteins/nucleic acids, has a similar structural role) as the reference sequence to which it is compared. Sequence identity/similarity is frequently employed as a criterion to identify candidate homologues. In the same vein, genetic sequences of the present invention have utility in identifying homologs in animals or other plant species, particularly those in the family Gramineae such as, but not limited to, sorghum, wheat, or rice. Function is frequently established on the basis of sequence identity/similarity.

Exemplary sequence comparison systems are provided for in sequence analysis software such as those provided by the Genetics Computer Group (Madison, Wis.) or InforMax (Bethesda, Md.), or Intelligenetics (Mountain View, Calif.). Optionally, sequence comparison is established using the BLAST or GAP suite of programs. Generally, a smallest sum probability value (P(N)) of less than 0.1, or alternatively, less than 0.01, 0.001, 0.0001, or 0.00001 using the BLAST 2.0 suite of algorithms under default parameters identifies the test sequence as a candidate homologue (i.e., an allele, ortholog, or paralog) of a reference sequence. Those of skill in the art will recognize that a candidate homologue has an increased statistical probability of having the same or similar function as the gene/protein represented by the test sequence.

The software/hardware for effecting identification, analysis, or modeling can be produced independently or obtained from commercial suppliers. Exemplary identification, analysis, and modeling tools are provided in products such as InforMax's (Bethesda, Md.) Vector NTI Suite (Version 5.5), Intelligenetics' (Mountain View, Calif.) PC/Gene program, and Genetics Computer Group's (Madison, Wis.) Wisconsin Package (Version 10.0); these tools, and the functions they perform, (as provided and disclosed by the programs and accompanying literature) are incorporated herein by reference.

Detection of Nucleic Acids

The present invention further provides methods for detecting a polynucleotide of the present invention in a nucleic acid sample suspected of containing a polynucleotide of the present invention, such as a plant cell lysate, particularly a lysate of maize. In some embodiments, a gene of the present invention or portion thereof can be amplified prior to the step of contacting the nucleic acid sample with a polynucleotide of the present invention. The nucleic acid sample is contacted with the polynucleotide to form a hybridization complex. The polynucleotide hybridizes under stringent conditions to a gene encoding a polypeptide of the present invention. Formation of the hybridization complex is used to detect a gene encoding a polypeptide of the present invention in the nucleic acid sample. Those of skill will appreciate that an isolated nucleic acid comprising a polynucleotide of the present invention should lack cross-hybridizing sequences in common with non-target genes that would yield a false positive result.

Detection of the hybridization complex can be achieved using any number of well known methods. For example, the nucleic acid sample, or a portion thereof, may be assayed by hybridization formats including but not limited to, solution phase, solid phase, mixed phase, or in situ hybridization assays. Briefly, in solution (or liquid) phase hybridizations, both the target nucleic acid and the probe or primer are free to interact in the reaction mixture. In solid phase hybridization assays, probes or primers are typically linked to a solid support where they are available for hybridization with target nucleic in solution. In mixed phase, nucleic acid intermediates in solution hybridize to target nucleic acids in solution as well as to a nucleic acid linked to a solid support. In in situ hybridization, the target nucleic acid is liberated from its cellular surroundings in such as to be available for hybridization within the cell while preserving the cellular morphology for subsequent interpretation and analysis. The following articles provide an overview of the various hybridization assay formats: Singer et al., *Biotechniques* 4(3): 230–250 (1986); Haase et al., *Methods in Virology*, Vol. VII, pp. 189–226 (1984); Wilkinson, The theory and practice of in situ hybridization in: *In situ Hybrdization*, D. G. Wilkinson, Ed., IRL Press, Oxford University Press, Oxford; and *Nucleic Acid Hybridization: A Practical Approach*, Hames, B. D. and Higgins, S. J., Eds., IRL Press (1987).

Nucleic Acid Labels and Detection Methods

The means by which nucleic acids of the present invention are labeled is not a critical aspect of the present invention and can be accomplished by any number of methods currently known or later developed. Detectable labels suitable for use in the present invention include any composition detectable by spectroscopic, radioisotopic, photochemical, biochemical, immunochemical, electrical, optical or chemical means. Useful labels in the present invention include biotin for staining with labeled streptavidin conjugate, magnetic beads, fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads.

Nucleic acids of the present invention can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include ligands which bind to antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation. Labeling the nucleic acids of the present invention is readily achieved such as by the use of labeled PCR primers.

In some embodiments, the label is simultaneously incorporated during the amplification step in the preparation of the nucleic acids. Thus, for example, polymerase chain reaction (PCR) with labeled primers or labeled nucleotides will provide a labeled amplification product. In another embodiment, transcription amplification using a labeled nucleotide (e.g., fluorescein-labeled UTP and/or CTP) incorporates a label into the transcribed nucleic acids.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned DNA probes have been coupled directly to horseradish peroxidase or alkaline phosphatase. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Antibodies to Proteins

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Many methods of making antibodies are known to persons of skill. A variety of analytic methods are available to generate a hydrophilicity profile of a protein of the present invention. Such methods can be used to guide the artisan in the selection of peptides of the present invention for use in the generation or selection of antibodies which are specifically reactive, under immunogenic conditions, to a protein of the present invention. See, e.g., J. Janin, *Nature,* 277 (1979) 491–492; Wolfenden, et al., *Biochemistry* 20(1981) 849–855; Kyte and Doolite, *J. Mol. Biol.* 157(1982) 105–132; Rose, et al., *Science* 229(1985) 834–838. The following discussion is presented as a general overview of the techniques available; however, one of skill will recognize that many variations upon the following methods are known.

A number of immunogens are used to produce antibodies specifically reactive with a protein of the present invention. An isolated recombinant, synthetic, or native polynucleotide of the present invention are the preferred antigens for the production of monoclonal or polyclonal antibodies. Polypeptides of the present invention are optionally denatured, and optionally reduced, prior to formation of antibodies for screening expression libraries or other assays in which a putative protein of the present invention is expressed or denatured in a non-native secondary, tertiary, or quartenary structure.

The protein of the present invention is then injected into an animal capable of producing antibodies. Either monoclonal or polyclonal antibodies can be generated for subsequent use in immunoassays to measure the presence and quantity of the protein of the present invention. Methods of producing polyclonal antibodies are known to those of skill in the art. In brief, an antigen, preferably a purified protein, a protein coupled to an appropriate carrier (e.g., GST, keyhole limpet hemanocyanin, etc.), or a protein incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the protein of interest. When appropriately high titers of antibody to the immunogen are obtained, blood is collected from the animal and antisera are prepared. Further fractionation of the antisera to enrich for antibodies reactive to the protein is performed where desired (See, e.g., Coligan, *Current Protocols in Immunology,* Wiley/Greene, NY (1991); and Harlow and Lane, *Antibodies: A Laboratory Manual,* Cold Spring Harbor Press, NY (1989)).

Antibodies, including binding fragments and single chain recombinant versions thereof, against predetermined fragments of a protein of the present invention are raised by immunizing animals, e.g., with conjugates of the fragments with carrier proteins as described above. Typically, the immunogen of interest is a protein of at least about 5 amino acids, more typically the protein is 10 amino acids in length, preferably, 15 amino acids in length and more preferably the protein is 20 amino acids in length or greater. The peptides are typically coupled to a carrier protein (e.g., as a fusion protein), or are recombinantly expressed in an immunization vector. Antigenic determinants on peptides to which antibodies bind are typically 3 to 10 amino acids in length.

Monoclonal antibodies are prepared from hyrbrid cells secreting the desired antibody. Monoclonals antibodies are screened for binding to a protein from which the antigen was derived. Specific monoclonal and polyclonal antibodies will usually have an antibody binding site with an affinity constant for its cognate monovalent antigen at least between $10^6$–$10^7$, usually at least $10^8$, preferably at least $10^9$, more preferably at least $10^{10}$, and most preferably at least $10^{11}$ liters/mole.

In some instances, it is desirable to prepare monoclonal antibodies from various mammalian hosts, such as mice, rodents, primates, humans, etc. Description of techniques for preparing such monoclonal antibodies are found in, e.g., *Basic and Clinical Immunology,* 4th ed., Stites et al., Eds., Lange Medical Publications, Los Altos, Calif., and references cited therein; Harlow and Lane, Supra; Goding, *Monoclonal Antibodies: Principles and Practice,* 2nd ed., Academic Press, New York, N.Y. (1986); and Kohler and Milstein, *Nature* 256: 495–497 (1975). Summarized briefly, this method proceeds by injecting an animal with an antigen comprising a protein of the present invention. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the antigen. In this manner, the individual antibody species obtained are the products of immortalized and cloned single B cells from the immune animal generated in response to a specific site recognized on the antigenic substance.

Other suitable techniques involve selection of libraries of recombinant antibodies in phage or similar vectors (see, e.g., Huse et al., Science 246: 1275–1281 (1989); and Ward, et al., Nature 341: 544–546 (1989); and Vaughan et al., Nature Biotechnology, 14: 309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., Nature Biotech., 14: 845–851 (1996). Also, recombinant immunoglobulins may be produced. See, Cabilly, U.S. Pat. No. 4,816,567; and Queen et al., Proc. Nat'l Acad. Sci. 86: 10029–10033 (1989).

The antibodies of this invention are also used for affinity chromatography in isolating proteins of the present invention. Columns are prepared, e.g., with the antibodies linked to a solid support, e.g., particles, such as agarose, SEPHADEX, or the like, where a cell lysate is passed through the column, washed, and treated with increasing concentrations of a mild denaturant, whereby purified protein are released.

The antibodies can be used to screen expression libraries for particular expression products such as normal or abnormal protein. Usually the antibodies in such a procedure are labeled with a moiety allowing easy detection of presence of antigen by antibody binding.

Antibodies raised against a protein of the present invention can also be used to raise anti-idiotypic antibodies. These are useful for detecting or diagnosing various pathological conditions related to the presence of the respective antigens.

Frequently, the proteins and antibodies of the present invention will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent moieties, chemiluminescent moieties, magnetic particles, and the like.

Although the present invention has been described in some detail by way of illustration and example for purposes of clarity of understanding, it will be obvious that certain changes and modifications may be practiced within the scope of the appended claims.

EXAMPLE 1

This example describes the construction of the cDNA libraries.

Total RNA Isolation

Total RNA was isolated from maize tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. Anal. Biochem. 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringency conditions and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm$^2$ agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm$^2$ nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook,J., Fritsch, E. F. and Maniatis, T., (in Molecular Cloning: A laboratory Manual, 2$^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire maize sequence database.
4. A Sal-A20 oligo nucleotide: TCG ACC CAC GCG TCC GAA AAA AAA AAA AAA AAA AAA, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search.

Gene identities were determined by conducting BLAST (Basic Local Alignment Search Tool; Altschul, S. F., et al., (1993) J. Mol. Biol. 215:403–410; see also www.ncbi.nlm.nih.gov/BLAST/) searches under default parameters for similarity to sequences contained in the BLAST "nr" database (comprising all non-redundant Gen-Bank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA were used to construct contiguous DNA sequences.

The prolifera gene in maize (SEQ ID NO:1) has 85.9% similarity and 80.6% identity to the previously reported Arabidopsis Prolifera gene (Springer, P. S., McCombie, W. R., Sundaresan, V., Martienssen, R. A. *Science* 268: 877–880 (1995) GenBank Accession L39954). Based upon its similarity to the Arabidopsis sequence, it appears that the maize sequence is MCM7 in the mcm2-3-5 family. Most MCM proteins share a conserved central region that contains a motif for NPT-binding (GXXGXGKS/T) which is also present in the maize sequence. This region originally was shown to have some similarity to two groups of prokaryotic ATPases: NtrC family of bacterial transcription factors and a set of proteins related to magnesium chelatases. The maize sequence also has the putative zinc-finger domain reported in some MCM proteins. Since only four of the MCM proteins, namely MCM2, MCM4, MCM6 and MCM7 have been reported to contain this zinc-finger type motif of the form $CX_2CX_{18-19}CX_{2-4}C$, the maize gene must be any of these four members. The top most hit in database searches was the known Arabidopsis prolifera gene in the public domain. Although both plant sequences (Maize and Arabidopsis) have similarity to other MCM proteins, albeit with significant divergence, it is safe to assume that plant sequences have diverged enough from other species. It is also significant to note that the conserved heptad repeat reported in other MCM protein is present in both the plant sequences. Overall both sequential and structural features as reported for other MCM proteins are conserved in plant sequences.

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is:

1. A data processing system having a memory and enabling programs to process data contained in said memory, comprising:

at least one data structure in said memory, said data structure supporting computer program access to data representing a genetic sequence, wherein said genetic sequence is: (i) a polynucleotide of at least 1500 contiguous nucleotides in length with at least 85% sequence identity to a polynucleotide sequence of SEQ ID NO: 1, or (ii) a polypeptide of at least 550 contiguous amino acids in length with at least 85% sequence identity to a polypeptide sequence of SEQ ID NO: 2, wherein sequence identity is determined by the GAP program under default parameters; and at least one genetic identification, analysis, or modeling computer program in said memory, said computer program directing the execution of instructions by said data processing system and using said genetic sequence to identify, analyze, or model at least one data element corresponding to a logical subcomponent of said genetic sequence.

2. The data processing system of claim 1, wherein said logical sub-component of said genetic sequence is a member selected from the group consisting of restriction enzyme sites, endopeptidase sites, major grooves, minor grooves, beta-sheet, alpha helices, ORFs, 5'UTRs, 3'UTRs, ribosome binding sites, glycosylation sites, signal peptide domains, intron-exon junctions, poly-A signals, transcription initiation sites, translation start sites, translation termination sites, methylation sites, zinc finger domains, modified amino acid sites, preproprotein-proprotein junctions, proprotein-protein junctions, transit peptide domains, SNPs, SSRs, RFLPs, insertion elements, transmembrane spanning regions and stem-loop structures.

3. A computer implemented process for identifying, analyzing, or modeling a genetic sequence, comprising:

providing a computer memory with data representing at least one genetic sequence, wherein said genetic sequence comprises: (i) a polynucleotide of at least 1500 contiguous nucleotides in length with at least 85% sequence identity to a polynucleotide sequence of SEQ ID NO: 1, or (ii) a polypeptide of at least 550 contiguous amino acids in length with at least 85% sequence identity to a polypeptide sequence of SEQ ID NO: 2, wherein sequence identity is determined by the GAP program under default parameters;

providing a computer program to identify, analyze or model at least one logical sub-component reflecting the higher order organization of said genetic sequence;

executing said computer program while granting said computer program access to said data representing said genetic sequence; and outputting results of said process.

4. The process of claim 3, further comprising isolating a nucleic acid comprising said genetic sequence from a nucleic acid library.

5. The process of claim 4, wherein said nucleic acid library is a full-length enriched cDNA library.

6. A data processing system, comprising: data representing at least one genetic sequence in a memory of said data processing system, wherein said genetic sequence is: (i) a polynucleotide of at least 1500 contiguous nucleotides in length with at least 85% sequence identity to a polynucleotide sequence of SEQ ID NO: 1, or (ii) a polypeptide of at least 550 contiguous amino acids in length with at least 85% sequence identity to a polypeptide sequence of SEQ ID NO: 2, wherein sequence identity is determined by the GAP program under default parameters;

a genetic identification, analysis, or modeling computer program designed to govern the processing of said data; and, a data processor having an output for storing or displaying data processing results, said data processor containing said data and said computer program and executing instructions according to said computer program to process said data or a contiguous subsequence thereof.

7. The data processing system of claim 6, wherein said data processing system is a distributed system having its input and output portions separated from at least some of its processing portions.

8. The data processing system of claim 7, wherein said data processing is distributed over an intranet, an internet, or both.

9. The data processing system of claim 6, wherein said program comprises at least one of:

a sequence similarity application, a protein structure application, a sequence alignment application, a translation application, a O-glycosylation prediction application, or a signal peptide prediction application.

10. The data processing system of claim 6, wherein said data processor stores said data in a memory while processing said data, and wherein successive portions of said data are copied sequentially into at least one register of said data processor where said portions are processed.

11. A memory for storing data that can be accessed by a computer programmed to implement a process for effecting the identification, analyses, or modeling of a sequence of a polynucleotide, said memory comprising data representing a polynucleotide of at least 1500 contiguous nucleotides in length with 85% sequence identity to the sequence of SEQ ID NO: 1, wherein sequence identity is determined by the GAP program under default parameters.

12. A memory for storing a data structure that can be accessed by a computer programmed to implement a process for effecting the identification, analysis, or modeling of a sequence of a polynucleotide, said memory comprising:

data stored within said memory representing a polynucleotide of at least 1500 contiguous nucleotides in length and having at least 85% sequence identity to the sequence of SEQ ID NO: 1, wherein said sequence identity is determined by the GAP program under default parameters, a data structure associated with said data and reflecting the underlying organization and structure of the data to facilitate computer program access to data elements corresponding to logical sub-components of the sequence, said data structure stored within said memory; and, said data structure enabling said polynucleotide to be identified and manipulated by said computer program.

13. A process for effecting the identification, analysis, or modeling of a polynucleotide sequence or its derived peptide sequence through use of a computer having a memory, said process comprising:

placing into said memory data representing a polynucleotide of at least 1500 contiguous nucleotides in length with 85% sequence identity to the sequence of SEQ ID NO: 1, wherein sequence identity is determined by the GAP program under default parameters, developing within said memory a data structure associated with said data and reflecting the underlying organization and structure of the data to facilitate a computer program access to data elements corresponding to logical sub-components of the sequence, programming said computer with said computer program containing instructions sufficient to implement the process for effecting the identification, analysis, or modeling of said polynucleotide sequence or said peptide sequence, and executing said computer program on said computer while granting said computer program access to said data and to said data structure within said memory.

14. A machine-readable media containing a computer program and data, comprising:

a computer program stored on said media containing instructions sufficient to implement a process for effecting the identification, analysis, or modeling of a representation of a polynucleotide or peptide sequence;

data stored on said media representing a sequence of a polynucleotide of at least 1500 contiguous nucleotides in length with at least 85% sequence identity to SEQ ID NO: 1, wherein sequence identity is determined by the GAP program under default parameters; and, a data structure reflecting the underlying organization and structure of said data to facilitate said computer program access to data elements corresponding to logical sub-components of the sequence, said data structure being inherent in said program and in the way in which said computer program organizes and accesses said data.

* * * * *

SEQUENCE LISTING

```
<160> NUMBER OF SEQ ID NOS:   2

<210> SEQ ID NO 1
<211> LENGTH: 2533
<212> TYPE: DNA
<213> ORGANISM: Zea mays
<220> FEATURE:
<221> NAME/KEY: CDS
<222> LOCATION: (110)...(2269)

<400> SEQUENCE: 1
ctttattccc ttcttcccgc catccccga acacttcgcc gccccctcc cgcctcccgc       60 tgttctctgc ctcccacccc cacgccgccg tcccatcacc gccgctggg atg aag aac   118
                                                     Met Lys Asn
                                                       1 cct gac ttc gcc gca gac aaa gcg ctc gcc aag gac ttc ctg tcc aat   166
Pro Asp Phe Ala Ala Asp Lys Ala Leu Ala Lys Asp Phe Leu Ser Asn
  5                  10                  15 ttc acc ggc cct cac ggc gag ccc aag tac ctg aac atc ctg caa gat   214
Phe Thr Gly Pro His Gly Glu Pro Lys Tyr Leu Asn Ile Leu Gln Asp
 20                  25                  30                  35 gtc gcg aac agg aag ata cgc gcg gtc cag atc gag ctg gac gac cta   262
Val Ala Asn Arg Lys Ile Arg Ala Val Gln Ile Glu Leu Asp Asp Leu
                 40                  45                  50 ttc cac tat aag gat gtc gac gag gag ttc ttg cag cgt gtc acc gag   310
Phe His Tyr Lys Asp Val Asp Glu Glu Phe Leu Gln Arg Val Thr Glu
             55                  60                  65 aac acg cgg cgc tac atc ggc atc ttc gcg gag gcc atg gac gag atc   358
Asn Thr Arg Arg Tyr Ile Gly Ile Phe Ala Glu Ala Met Asp Glu Ile
         70                  75                  80
```

```
atg ccg gag ccc aca gag gcg tac acc gtc gac gag gac cag gac atc    406
Met Pro Glu Pro Thr Glu Ala Tyr Thr Val Asp Glu Asp Gln Asp Ile
    85                  90                  95 ctg atg acg cag cgt gtg gat gag ggg gcc gac ggc ggc gcg gac ggc    454
Leu Met Thr Gln Arg Val Asp Glu Gly Ala Asp Gly Gly Ala Asp Gly
100                 105                 110                 115 acg gac ccg cta cag aaa atg cca cca gag atc aaa cgg ttc ttt gag    502
Thr Asp Pro Leu Gln Lys Met Pro Pro Glu Ile Lys Arg Phe Phe Glu
                120                 125                 130 gtt tac atc aag gca ttc tca aag gtg act cca ctc acc att cgg caa    550
Val Tyr Ile Lys Ala Phe Ser Lys Val Thr Pro Leu Thr Ile Arg Gln
            135                 140                 145 gtg aag gca tcc aac att ggt cag ctt gtg aaa ata tct ggg att gtt    598
Val Lys Ala Ser Asn Ile Gly Gln Leu Val Lys Ile Ser Gly Ile Val
        150                 155                 160 act cgc tgc tcg gat gtg aag ccc ttg atg cag gtt gct gtt tat aca    646
Thr Arg Cys Ser Asp Val Lys Pro Leu Met Gln Val Ala Val Tyr Thr
    165                 170                 175 tgt gaa gaa tgt ggc ttc gag ata tac cag gaa gtg act gct aga gtg    694
Cys Glu Glu Cys Gly Phe Glu Ile Tyr Gln Glu Val Thr Ala Arg Val
180                 185                 190                 195 ttt atg ccc ctc att gaa tgt cca tct caa cga tgc aag ctg aac aaa    742
Phe Met Pro Leu Ile Glu Cys Pro Ser Gln Arg Cys Lys Leu Asn Lys
                200                 205                 210 gcg aag gga aat cta atc ctt caa ctg cgt gcg tca aag ttt ttg aaa    790
Ala Lys Gly Asn Leu Ile Leu Gln Leu Arg Ala Ser Lys Phe Leu Lys
            215                 220                 225 ttt cag gag gta aag ctt caa gag tta gca gag cac gta cca aag ggc    838
Phe Gln Glu Val Lys Leu Gln Glu Leu Ala Glu His Val Pro Lys Gly
        230                 235                 240 cac att cct cgt gct ctg act gtt cat cta aga gga gag ctg act aga    886
His Ile Pro Arg Ala Leu Thr Val His Leu Arg Gly Glu Leu Thr Arg
    245                 250                 255 aag gtt gca cct gga gat gtg gtt gag atg tcg ggt att ttt ctc cct    934
Lys Val Ala Pro Gly Asp Val Val Glu Met Ser Gly Ile Phe Leu Pro
260                 265                 270                 275 atg cca tac tac ggg ttt aga gcg atg cgc gca gga tta gtt gct gat    982
Met Pro Tyr Tyr Gly Phe Arg Ala Met Arg Ala Gly Leu Val Ala Asp
                280                 285                 290 act tac ttg gaa gca atg tct gtc acc cac ttc aag aaa aaa tat gag   1030
Thr Tyr Leu Glu Ala Met Ser Val Thr His Phe Lys Lys Lys Tyr Glu
            295                 300                 305 gag tat gat cta aaa ggt gat gaa caa gaa caa att gac cga ttg gct   1078
Glu Tyr Asp Leu Lys Gly Asp Glu Gln Glu Gln Ile Asp Arg Leu Ala
        310                 315                 320 gag gac ggt gat atc tac agt aag ctg gca agg tcc ttg gca cct gaa   1126
Glu Asp Gly Asp Ile Tyr Ser Lys Leu Ala Arg Ser Leu Ala Pro Glu
    325                 330                 335 ata ttt ggc cat gaa gat gtc aaa aag gca ctg ctg tta cta ctt gtt   1174
Ile Phe Gly His Glu Asp Val Lys Lys Ala Leu Leu Leu Leu Leu Val
340                 345                 350                 355 ggt gca ccc cat cgg aag ctc gca gat ggc atg aag atc aga gga gac   1222
Gly Ala Pro His Arg Lys Leu Ala Asp Gly Met Lys Ile Arg Gly Asp
                360                 365                 370 ctg cat ata tgc atg atg gga gat cct ggt gtt gca aag agt caa ctt   1270
Leu His Ile Cys Met Met Gly Asp Pro Gly Val Ala Lys Ser Gln Leu
            375                 380                 385 ctg aag cat att atc aat gtt gca cca aga gga gtg tac acc act gga   1318
Leu Lys His Ile Ile Asn Val Ala Pro Arg Gly Val Tyr Thr Thr Gly
```

-continued

|     |     |     |     | 390 |     |     |     |     | 395 |     |     |     |     | 400 |     |      |
|-----|-----|-----|-----|-----|-----|-----|-----|-----|-----|-----|-----|-----|-----|-----|-----|------|
| cgt | ggg | agc | agt | ggt | gtt | gga | ctt | acc | gct | gca | gtc | cag | aaa | gat | cca | 1366 |
| Arg | Gly | Ser | Ser | Gly | Val | Gly | Leu | Thr | Ala | Ala | Val | Gln | Lys | Asp | Pro |      |
|     | 405 |     |     |     |     | 410 |     |     |     |     | 415 |     |     |     |     |      |

| gta | aca | aat | gag | ttt | gtc | ctc | gaa | ggt | gga | gca | ctg | gta | ctg | gca | gat | 1414 |
|-----|-----|-----|-----|-----|-----|-----|-----|-----|-----|-----|-----|-----|-----|-----|-----|------|
| Val | Thr | Asn | Glu | Phe | Val | Leu | Glu | Gly | Gly | Ala | Leu | Val | Leu | Ala | Asp |      |
| 420 |     |     |     |     | 425 |     |     |     |     | 430 |     |     |     |     | 435 |      |

| atg | ggc | att | tgt | gct | ata | gat | gag | ttt | gac | aag | atg | gaa | gag | tca | gac | 1462 |
|-----|-----|-----|-----|-----|-----|-----|-----|-----|-----|-----|-----|-----|-----|-----|-----|------|
| Met | Gly | Ile | Cys | Ala | Ile | Asp | Glu | Phe | Asp | Lys | Met | Glu | Glu | Ser | Asp |      |
|     |     |     |     | 440 |     |     |     |     | 445 |     |     |     |     | 450 |     |      |

| agg | aca | gcg | att | cat | gag | gta | atg | gag | cag | caa | aca | gtt | agc | att | gcc | 1510 |
|-----|-----|-----|-----|-----|-----|-----|-----|-----|-----|-----|-----|-----|-----|-----|-----|------|
| Arg | Thr | Ala | Ile | His | Glu | Val | Met | Glu | Gln | Gln | Thr | Val | Ser | Ile | Ala |      |
|     |     |     | 455 |     |     |     |     | 460 |     |     |     |     | 465 |     |     |      |

| aag | gct | ggc | atc | acc | acc | tct | ctt | aat | gcg | aga | act | gca | att | ctg | gct | 1558 |
|-----|-----|-----|-----|-----|-----|-----|-----|-----|-----|-----|-----|-----|-----|-----|-----|------|
| Lys | Ala | Gly | Ile | Thr | Thr | Ser | Leu | Asn | Ala | Arg | Thr | Ala | Ile | Leu | Ala |      |
|     |     | 470 |     |     |     |     | 475 |     |     |     |     | 480 |     |     |     |      |

| gct | gca | aat | cca | gca | tgg | gga | agg | tat | gat | atg | agg | aga | acc | cca | gca | 1606 |
|-----|-----|-----|-----|-----|-----|-----|-----|-----|-----|-----|-----|-----|-----|-----|-----|------|
| Ala | Ala | Asn | Pro | Ala | Trp | Gly | Arg | Tyr | Asp | Met | Arg | Arg | Thr | Pro | Ala |      |
|     | 485 |     |     |     |     | 490 |     |     |     |     | 495 |     |     |     |     |      |

| gaa | aat | ata | aat | cta | cct | cca | gct | ctt | ctg | tct | cgt | ttc | gac | ctc | ctt | 1654 |
|-----|-----|-----|-----|-----|-----|-----|-----|-----|-----|-----|-----|-----|-----|-----|-----|------|
| Glu | Asn | Ile | Asn | Leu | Pro | Pro | Ala | Leu | Leu | Ser | Arg | Phe | Asp | Leu | Leu |      |
| 500 |     |     |     |     | 505 |     |     |     |     | 510 |     |     |     |     | 515 |      |

| tgg | tta | atc | ctg | gat | cgt | gca | gac | atg | gaa | act | gat | ctt | gaa | atg | gca | 1702 |
|-----|-----|-----|-----|-----|-----|-----|-----|-----|-----|-----|-----|-----|-----|-----|-----|------|
| Trp | Leu | Ile | Leu | Asp | Arg | Ala | Asp | Met | Glu | Thr | Asp | Leu | Glu | Met | Ala |      |
|     |     |     |     | 520 |     |     |     |     | 525 |     |     |     |     | 530 |     |      |

| aga | cac | gtt | gtt | cat | gtg | cat | caa | aat | ctt | gaa | tca | cca | gcg | ctg | ggg | 1750 |
|-----|-----|-----|-----|-----|-----|-----|-----|-----|-----|-----|-----|-----|-----|-----|-----|------|
| Arg | His | Val | Val | His | Val | His | Gln | Asn | Leu | Glu | Ser | Pro | Ala | Leu | Gly |      |
|     |     |     | 535 |     |     |     |     | 540 |     |     |     |     | 545 |     |     |      |

| ttc | aca | cca | ctt | gag | cca | tct | gta | ctc | aga | gca | tac | ata | tct | gct | gct | 1798 |
|-----|-----|-----|-----|-----|-----|-----|-----|-----|-----|-----|-----|-----|-----|-----|-----|------|
| Phe | Thr | Pro | Leu | Glu | Pro | Ser | Val | Leu | Arg | Ala | Tyr | Ile | Ser | Ala | Ala |      |
|     |     | 550 |     |     |     |     | 555 |     |     |     |     | 560 |     |     |     |      |

| aga | aga | gtc | att | cct | tct | gtt | cct | aga | gag | ctc | gag | gaa | tac | att | gca | 1846 |
|-----|-----|-----|-----|-----|-----|-----|-----|-----|-----|-----|-----|-----|-----|-----|-----|------|
| Arg | Arg | Val | Ile | Pro | Ser | Val | Pro | Arg | Glu | Leu | Glu | Glu | Tyr | Ile | Ala |      |
|     | 565 |     |     |     |     | 570 |     |     |     |     | 575 |     |     |     |     |      |

| act | gca | tat | tcc | agc | atc | cgc | caa | gag | gag | gcg | aag | tca | aat | gca | cca | 1894 |
|-----|-----|-----|-----|-----|-----|-----|-----|-----|-----|-----|-----|-----|-----|-----|-----|------|
| Thr | Ala | Tyr | Ser | Ser | Ile | Arg | Gln | Glu | Glu | Ala | Lys | Ser | Asn | Ala | Pro |      |
| 580 |     |     |     |     | 585 |     |     |     |     | 590 |     |     |     |     | 595 |      |

| acc | tcc | tac | aca | act | atc | aga | aca | ctt | ttg | agc | ata | ctc | cgt | atc | tct | 1942 |
|-----|-----|-----|-----|-----|-----|-----|-----|-----|-----|-----|-----|-----|-----|-----|-----|------|
| Thr | Ser | Tyr | Thr | Thr | Ile | Arg | Thr | Leu | Leu | Ser | Ile | Leu | Arg | Ile | Ser |      |
|     |     |     |     | 600 |     |     |     |     | 605 |     |     |     |     | 610 |     |      |

| att | gcc | ttg | gca | aga | ctg | agg | ttc | tca | gaa | act | gtg | gct | cag | agc | gat | 1990 |
|-----|-----|-----|-----|-----|-----|-----|-----|-----|-----|-----|-----|-----|-----|-----|-----|------|
| Ile | Ala | Leu | Ala | Arg | Leu | Arg | Phe | Ser | Glu | Thr | Val | Ala | Gln | Ser | Asp |      |
|     |     |     | 615 |     |     |     |     | 620 |     |     |     |     | 625 |     |     |      |

| gtc | gac | gaa | gca | ctg | cga | ctg | atg | caa | atg | tcc | aag | tac | tca | tta | tac | 2038 |
|-----|-----|-----|-----|-----|-----|-----|-----|-----|-----|-----|-----|-----|-----|-----|-----|------|
| Val | Asp | Glu | Ala | Leu | Arg | Leu | Met | Gln | Met | Ser | Lys | Tyr | Ser | Leu | Tyr |      |
|     | 630 |     |     |     |     | 635 |     |     |     |     | 640 |     |     |     |     |      |

| tca | gat | gac | cgc | cag | cgg | tct | ggc | ctt | gat | gca | ata | tct | gac | ata | tat | 2086 |
|-----|-----|-----|-----|-----|-----|-----|-----|-----|-----|-----|-----|-----|-----|-----|-----|------|
| Ser | Asp | Asp | Arg | Gln | Arg | Ser | Gly | Leu | Asp | Ala | Ile | Ser | Asp | Ile | Tyr |      |
|     | 645 |     |     |     |     | 650 |     |     |     |     | 655 |     |     |     |     |      |

| tcc | atc | ctg | aga | gac | gaa | gct | gct | agg | acg | agc | agc | atg | gat | gtg | aga | 2134 |
|-----|-----|-----|-----|-----|-----|-----|-----|-----|-----|-----|-----|-----|-----|-----|-----|------|
| Ser | Ile | Leu | Arg | Asp | Glu | Ala | Ala | Arg | Thr | Ser | Ser | Met | Asp | Val | Arg |      |
| 660 |     |     |     |     | 665 |     |     |     |     | 670 |     |     |     |     | 675 |      |

| tac | gct | cac | gct | ctt | aac | ttg | atc | tcc | aga | aag | gga | tac | agc | gag | gct | 2182 |
|-----|-----|-----|-----|-----|-----|-----|-----|-----|-----|-----|-----|-----|-----|-----|-----|------|
| Tyr | Ala | His | Ala | Leu | Asn | Leu | Ile | Ser | Arg | Lys | Gly | Tyr | Ser | Glu | Ala |      |
|     |     |     |     | 680 |     |     |     |     | 685 |     |     |     |     | 690 |     |      |

| caa | ttg | aag | gaa | tgc | ttg | gag | gaa | tac | gct | tcc | ctg | aat | gtg | tgg | cag | 2230 |
|-----|-----|-----|-----|-----|-----|-----|-----|-----|-----|-----|-----|-----|-----|-----|-----|------|
| Gln | Leu | Lys | Glu | Cys | Leu | Glu | Glu | Tyr | Ala | Ser | Leu | Asn | Val | Trp | Gln |      |
|     |     |     | 695 |     |     |     |     | 700 |     |     |     |     | 705 |     |     |      |

| atc | cat | cca | agc | aca | ttt | gac | atc | cac | ttc | att | gat | gcc | tgatgcagaa |     |     | 2279 |
|-----|-----|-----|-----|-----|-----|-----|-----|-----|-----|-----|-----|-----|------------|-----|-----|------|

```
Ile His Pro Ser Thr Phe Asp Ile His Phe Ile Asp Ala
            710                 715                 720 gccgatgccg atcacctaac atttcatcat gatccaagga tttgaagacc ttcgactgaa      2339
gcctaacaag atttaaaagt tttctagtga tagtgaacga cagcccattt cttgatggca      2399
atgatgtaat gctgagaagc ctatctcaat tgcactagta gaaacaatct caattgtact      2459
agaagaacca ttcttgtatg acttgtgagt agcttgtttt tatatttgct gacaaaaaaa      2519
aaaaaaaaaa aaaa                                                         2533

<210> SEQ ID NO 2
<211> LENGTH: 720
<212> TYPE: PRT
<213> ORGANISM: Zea mays

<400> SEQUENCE: 2

Met Lys Asn Pro Asp Phe Ala Ala Asp Lys Ala Leu Ala Lys Asp Phe
  1               5                  10                  15

Leu Ser Asn Phe Thr Gly Pro His Gly Glu Pro Lys Tyr Leu Asn Ile
             20                  25                  30

Leu Gln Asp Val Ala Asn Arg Lys Ile Arg Ala Val Gln Ile Glu Leu
         35                  40                  45

Asp Asp Leu Phe His Tyr Lys Asp Val Asp Glu Phe Leu Gln Arg
     50                  55                  60

Val Thr Glu Asn Thr Arg Arg Tyr Ile Gly Ile Phe Ala Glu Ala Met
 65                  70                  75                  80

Asp Glu Ile Met Pro Glu Pro Thr Glu Ala Tyr Thr Val Asp Glu Asp
                 85                  90                  95

Gln Asp Ile Leu Met Thr Gln Arg Val Asp Glu Gly Ala Asp Gly Gly
             100                 105                 110

Ala Asp Gly Thr Asp Pro Leu Gln Lys Met Pro Pro Glu Ile Lys Arg
         115                 120                 125

Phe Phe Glu Val Tyr Ile Lys Ala Phe Ser Lys Val Thr Pro Leu Thr
    130                 135                 140

Ile Arg Gln Val Lys Ala Ser Asn Ile Gly Gln Leu Val Lys Ile Ser
145                 150                 155                 160

Gly Ile Val Thr Arg Cys Ser Asp Val Lys Pro Leu Met Gln Val Ala
                165                 170                 175

Val Tyr Thr Cys Glu Glu Cys Gly Phe Glu Ile Tyr Gln Glu Val Thr
            180                 185                 190

Ala Arg Val Phe Met Pro Leu Ile Glu Cys Pro Ser Gln Arg Cys Lys
        195                 200                 205

Leu Asn Lys Ala Lys Gly Asn Leu Ile Leu Gln Leu Arg Ala Ser Lys
    210                 215                 220

Phe Leu Lys Phe Gln Glu Val Lys Leu Gln Glu Leu Ala Glu His Val
225                 230                 235                 240

Pro Lys Gly His Ile Pro Arg Ala Leu Thr Val His Leu Arg Gly Glu
                245                 250                 255

Leu Thr Arg Lys Val Ala Pro Gly Asp Val Val Glu Met Ser Gly Ile
            260                 265                 270

Phe Leu Pro Met Pro Tyr Tyr Gly Phe Arg Ala Met Arg Ala Gly Leu
        275                 280                 285

Val Ala Asp Thr Tyr Leu Glu Ala Met Ser Val Thr His Phe Lys Lys
    290                 295                 300

Lys Tyr Glu Glu Tyr Asp Leu Lys Gly Asp Glu Gln Glu Gln Ile Asp
```

-continued

```
305                 310                 315                 320

Arg Leu Ala Glu Asp Gly Asp Ile Tyr Ser Lys Leu Ala Arg Ser Leu
                325                 330                 335

Ala Pro Glu Ile Phe Gly His Glu Asp Val Lys Ala Leu Leu Leu
                340                 345                 350

Leu Leu Val Gly Ala Pro His Arg Lys Leu Ala Asp Gly Met Lys Ile
            355                 360                 365

Arg Gly Asp Leu His Ile Cys Met Met Gly Asp Pro Gly Val Ala Lys
        370                 375                 380

Ser Gln Leu Leu Lys His Ile Ile Asn Val Ala Pro Arg Gly Val Tyr
385                 390                 395                 400

Thr Thr Gly Arg Gly Ser Ser Gly Val Gly Leu Thr Ala Ala Val Gln
                405                 410                 415

Lys Asp Pro Val Thr Asn Glu Phe Val Leu Glu Gly Gly Ala Leu Val
            420                 425                 430

Leu Ala Asp Met Gly Ile Cys Ala Ile Asp Glu Phe Asp Lys Met Glu
        435                 440                 445

Glu Ser Asp Arg Thr Ala Ile His Glu Val Met Glu Gln Gln Thr Val
    450                 455                 460

Ser Ile Ala Lys Ala Gly Ile Thr Thr Ser Leu Asn Ala Arg Thr Ala
465                 470                 475                 480

Ile Leu Ala Ala Ala Asn Pro Ala Trp Gly Arg Tyr Asp Met Arg Arg
                485                 490                 495

Thr Pro Ala Glu Asn Ile Asn Leu Pro Pro Ala Leu Leu Ser Arg Phe
            500                 505                 510

Asp Leu Leu Trp Leu Ile Leu Asp Arg Ala Asp Met Glu Thr Asp Leu
        515                 520                 525

Glu Met Ala Arg His Val Val His Val His Gln Asn Leu Glu Ser Pro
    530                 535                 540

Ala Leu Gly Phe Thr Pro Leu Glu Pro Ser Val Leu Arg Ala Tyr Ile
545                 550                 555                 560

Ser Ala Ala Arg Arg Val Ile Pro Ser Val Pro Arg Glu Leu Glu Glu
                565                 570                 575

Tyr Ile Ala Thr Ala Tyr Ser Ser Ile Arg Gln Glu Glu Ala Lys Ser
            580                 585                 590

Asn Ala Pro Thr Ser Tyr Thr Thr Ile Arg Thr Leu Leu Ser Ile Leu
        595                 600                 605

Arg Ile Ser Ile Ala Leu Ala Arg Leu Arg Phe Ser Glu Thr Val Ala
    610                 615                 620

Gln Ser Asp Val Asp Glu Ala Leu Arg Leu Met Gln Met Ser Lys Tyr
625                 630                 635                 640

Ser Leu Tyr Ser Asp Asp Arg Gln Arg Ser Gly Leu Asp Ala Ile Ser
                645                 650                 655

Asp Ile Tyr Ser Ile Leu Arg Asp Glu Ala Ala Arg Thr Ser Ser Met
            660                 665                 670

Asp Val Arg Tyr Ala His Ala Leu Asn Leu Ile Ser Arg Lys Gly Tyr
        675                 680                 685

Ser Glu Ala Gln Leu Lys Glu Cys Leu Glu Glu Tyr Ala Ser Leu Asn
    690                 695                 700

Val Trp Gln Ile His Pro Ser Thr Phe Asp Ile His Phe Ile Asp Ala
705                 710                 715                 720
```